(12) United States Patent
Garbos et al.

(10) Patent No.: US 9,528,877 B2
(45) Date of Patent: Dec. 27, 2016

(54) SPECTROMETER AND A FLUID ANALYSIS SYSTEM (71) Applicant: Buerkert Werke GmbH, Ingelfingen (DE)

(72) Inventors: Martin Garbos, Wuerzburg (DE); Christoph Scholl, Neuenstein (DE)

(73) Assignee: BUERKERT WERKE GMBH (DE)

( * ) Notice: Subject to any disclaimer, the term of this patent is extended or adjusted under 35 U.S.C. 154(b) by 0 days.

(21) Appl. No.: 14/607,745

(22) Filed: Jan. 28, 2015

(65) Prior Publication Data
US 2015/0219495 A1 Aug. 6, 2015

(30) Foreign Application Priority Data

Feb. 3, 2014 (DE) .................. 10 2014 101 269
Jan. 13, 2015 (DE) .................. 10 2015 100 395

(51) Int. Cl.
*G01J 3/28* (2006.01)
*G01J 3/02* (2006.01)
*G01N 21/25* (2006.01)
*G01J 3/18* (2006.01)
*G01J 3/04* (2006.01)
*G01N 21/85* (2006.01)

(52) U.S. Cl.
CPC ............... *G01J 3/28* (2013.01); *G01J 3/0208* (2013.01); *G01J 3/04* (2013.01); *G01J 3/18* (2013.01); *G01J 2003/2866* (2013.01); *G01N 21/255* (2013.01); *G01N 21/85* (2013.01); *G01N 2201/061* (2013.01); *G01N 2201/068* (2013.01)

(58) Field of Classification Search
CPC ............... G01J 3/04; G01J 3/0208; G01J 3/18
See application file for complete search history.

(56) References Cited

U.S. PATENT DOCUMENTS

| 5,680,209 | A  | * | 10/1997 | Machler | .................. | G01J 3/02 250/373 |
| 6,839,140 | B1 | * | 1/2005  | O'Keefe | ................ | G01N 21/31 356/436 |
| 7,554,667 | B1 | * | 6/2009  | Kampe   | .................... | G01J 3/26 356/328 |
| 2005/0243312 | A1 | * | 11/2005 | Geshwind | ................ | G01J 3/02 356/310 |

(Continued)

FOREIGN PATENT DOCUMENTS

| DE | 102 55 022 | 6/2004 | ................ G01J 3/42 |
| EP | 0 772 029  | 5/1997 | ................ G01J 3/02 |

OTHER PUBLICATIONS

German Search Report issued in corresponding German Patent Appln. Serial No. 10 2014 101 269.0 dated Nov. 14, 2014 (7 pgs).

*Primary Examiner* — Kara E Geisel
*Assistant Examiner* — Dominic J Bologna
(74) *Attorney, Agent, or Firm* — Hayes Soloway P.C.

(57) ABSTRACT

A spectrometer, in particular for being installed in a sensor module of a fluid analysis system, including a radiation source and the following components defining a beam path or being arranged along the beam path: a sample chamber for a fluid to be examined, a first lens, a diffraction element, a second lens and a detector. A restriction aperture for restricting the effective diameter of the light beam incident on the diffraction element is provided between the sample chamber and the diffraction element.

26 Claims, 10 Drawing Sheets

(56) References Cited

U.S. PATENT DOCUMENTS

| | | | |
|---|---|---|---|
| 2006/0072117 A1* | 4/2006 | Ruth | G01J 3/42 |
| | | | 356/453 |
| 2009/0250595 A1* | 10/2009 | Kalitsis | G01N 21/3563 |
| | | | 250/208.2 |
| 2011/0080583 A1* | 4/2011 | Rabus | G01J 3/02 |
| | | | 356/328 |
| 2012/0293798 A1* | 11/2012 | Song | G01N 1/125 |
| | | | 356/326 |
| 2014/0002820 A1* | 1/2014 | Ko | G01J 3/0256 |
| | | | 356/328 |
| 2015/0000384 A1* | 1/2015 | Chekalyuk | G01N 21/6408 |
| | | | 73/61.48 |

* cited by examiner

SPECTROMETER AND A FLUID ANALYSIS SYSTEM

TECHNICAL FIELD

The invention relates to a spectrometer, in particular for being installed in a sensor module of a fluid analysis system. The invention further relates to a fluid analysis system including such a spectrometer.

BACKGROUND OF THE INVENTION

Spectrometers are of great importance for the analysis of fluids, especially (drinking) water, because they allow measurements of important parameters to be carried out in a contact-free manner and either with or without the addition of additives. This includes, for example, the measurement of the spectral absorption coefficient (SAC), at 254 nm, or the measurement of the total organic carbon (TOC) content.

There is a demand for analytical apparatuses including several and/or replaceable sensor modules, which should be as small as possible. However, the compact design of spectrometers with low-cost components (lenses, gratings and apertures) comes with certain disadvantages. One particular problem is the extensive curvature of the image field, on which the spectrum is imaged. The extensive curvature is a consequence of the limited installation space, which requires lenses having limited focal lengths and thus small lens radii.

It is an object of the invention to provide a compact spectrometer having an improved resolution of the imaged spectrum.

BRIEF SUMMARY OF THE INVENTION

According to the invention, a spectrometer, in particular for being installed in a sensor module, includes a radiation source and the following components which define a beam path or are arranged along the beam path: a sample chamber for a fluid to be examined, a first lens, a diffraction element, a second lens and a detector. A restriction aperture for restricting the effective diameter of the beam incident on the diffraction element is provided between the sample chamber and the diffraction element.

With regard to the beam path extending from the radiation source, the components mentioned are preferably arranged in the order specified above, with the restriction aperture being located either in front of or behind the first lens, which will be explained in more detail later. Of course, the spectrometer may include further components without deviating from the scope of the invention.

Irrespective of the wavelength of the radiation emitted by the radiation source, the terms "radiation" and "light" will hereinafter be used synonymously.

As a sample chamber for the fluid to be examined, the inner space of a cuvette, a media passage or any other suitable container for receiving the fluid may be used, through which the fluid can preferably flow.

The lenses of the spectrometer according to the invention are in particular convex lenses, i.e. lenses having a positive refractive power, preferably plano-convex lenses that convert a parallel beam into a convergent beam.

As a diffractive element, in particular a reflection grating, a transmission grating or a prism is considered.

The effective diameter of the light beam incident on the diffractive element is viewed in a plane that is perpendicular to the optical axis, with the optical axis being defined for example by an entrance aperture which is placed between the radiation source and the sample chamber and the first lens, or by the first lens on its own, and determines, at least up to the diffractive element, the main direction of the beam path. More specifically, what is regarded as the effective diameter is the maximum width of the beam in the direction in which the spectral components are split (possibly after having been deflected), irrespective of whether the beam cross section is circular, oval or of a different shape.

The invention is based on the finding that a very good resolution can be achieved also with a small spectrometer having simple (low-cost) components. According to the invention, it is the restriction aperture that is responsible for the enhanced resolution, by limiting the effective diameter of the beam incident on the diffractive element. As with any established optical spectrometer, the light incident on the diffractive element is split into its spectral colors by the diffractive element and is then focussed by the second lens onto a detector that is sensitive to the light of the relevant wavelength range. The restricting aperture ensures that only a very narrow beam is incident on the diffractive element. As a result, the optical errors in the detector plane caused by the inevitable curvature of the image field are greatly reduced, i.e. the resolution or sharpness of the imaged spectrum is substantially enhanced. Further imaging errors, such as chromatic or spherical aberration, are also greatly reduced.

In order to achieve a significant improvement of the resolution, in particular if a first lens having a relatively large diameter is used, the width of the restriction aperture should in this case be considerably smaller than the diameter of the first lens.

For the preferred applications of the invention, a width of the restriction aperture has proven to be useful that is in a range between 0.1 and 1.5 mm, preferably between 0.1 and 1.0 mm.

According to a preferred embodiment of the invention, the focal length of the first lens is in the range of centimeters, preferably between 3 and 7 cm. The focal length of the second lens is also in the range of centimeters, preferably between 2 and 5 cm.

The improvement of the resolution correlates with a sharpening factor that is defined as $S=R_B/d$, wherein $R_B$=image field radius and d=width of the restriction aperture. To achieve useful results, the sharpening factor should in any case be greater than 10 and is preferably in a range between 30 and 70.

As has already been mentioned above, in principle there are two possibilities for positioning the restriction aperture. The first possibility provides for a positioning of the restriction aperture between the first lens and the diffraction element. In this area behind the first lens, which is also referred to as Fourier space, the light of the radiation source is collimated. Therefore, the distance between the restriction aperture and the collimation lens can basically be chosen as desired, which allows more freedom in design.

For example, the restriction aperture may be formed by a narrow light channel in a component that preferably also serves as a holder for the first lens. In this case, the component fulfils a dual function.

According to a particularly space-saving embodiment, the restriction aperture is formed in a layer that is applied on the side of the first lens that faces the diffraction element, i.e. the layer is interrupted at the location of the restriction aperture.

The second possibility for the placement of the restriction aperture provides for the latter to be located in the beam path immediately in front of the first lens. In this case, the restriction aperture should be located as closely as possible to the first lens, because here the light of the radiation source has not yet been collimated by the first lens.

The restriction aperture in turn may be formed in a place-saving manner in a layer applied on the side of the first lens that faces the sample chamber, i.e. the layer is interrupted at the location of the restriction aperture.

If an extremely small first lens is used, for example in a range between 0.1 and 1.5 mm, preferably between 0.1 and 1.0 mm, the restriction aperture may be simply formed by a holder that directly surrounds the first lens.

As a detector, preferably a linear detector, in particular a line sensor is used, since such a detector requires only little installation space and an extensive two-dimensional detector for acquiring the spectrum is not absolutely necessary.

According to a preferred embodiment of the invention, the maximum extension of the optically sensitive range of the detector is in the range of centimeters, preferably between 1 and 4 cm.

For applications in the field of water analysis, where the substances to be detected are present only in very small concentrations, it is required or at least advantageous if the light of the radiation source takes a path through the fluid that is as long as possible. Therefore, the sample chamber should, in the direction of the beam path, have a length of several centimeters, preferably of more than 4 cm.

In order to analyze flowing fluids a design is advantageous where the sample chamber is connected to an inflow channel and an outflow channel, which preferably both open into the sample chamber via ring lines, with the ring lines being formed in a housing that surrounds the sample chamber.

The diffraction element of the spectrometer according to the invention is preferably implemented as a mirror grating. Apart from the diffraction required for the analysis, the mirror grating additionally provides for a deflection of the beam. By means of a suitable arrangement of the mirror grating, the subsequent components can be arranged next to the preceding components, so that the installation space can be reduced in the direction of the optical axis. The diffraction element can also be a diffraction grating coated with a suitable splitting geometry or may be formed to be only as narrow as a gap would be wide.

For many applications, a xenon flash lamp, the light of which spans the range from UV into infrared, is suitable as a radiation source.

According to a first type of design of the spectrometer according to the invention, an entrance aperture is additionally provided in the beam path, preferably more or less immediately behind the radiation source. The entrance aperture ensures that the light used for the measurements will always enter the spectrometer at exactly the same location.

A particularly compact design is achieved by means of an arrangement in which the sample chamber is located in the beam path behind the entrance aperture. Thus, the sample chamber is integrated into the actual spectrometer, as a result of which the overall size of the design is reduced.

The invention also provides a fluid analysis system having a spectrometer of the kind mentioned above.

If the spectrometer according to the first design type mentioned above has an entrance aperture, then this has the disadvantage that the entrance aperture has to be exactly aligned relative to the radiation source, which requires a corresponding assembly effort. In a particular development of the invention, the design of the spectrometer according to the invention is simplified in this respect. According to this simplified second type of design, no entrance aperture is provided between the radiation source and the sample chamber of the spectrometer. However, in this case the fluid analysis system includes an electronic unit that is designed to take into account a shift of the spectra acquired by the detector during the evaluation of multiple (consecutive) measurements. Thus, the absent entrance aperture and its alignment are replaced with a computational procedure.

Preferably, an initial calibration is carried out by associating a characteristic maximum of the spectrum with a pixel of a sensor of the detector. On the basis of this pixel, further pixels of the sensor are permanently associated with corresponding wavelengths.

Ideally, each measurement is individually calibrated and/or corrected on the basis of a selected characteristic range of the detected spectrum in the form of an evaluation window that is defined by a wavelength range or a pixel area of the sensor, which corresponds to the wavelength range, and by an intensity range.

In most cases it is the simplest option to calculate a shift between the various measurements on the basis of the position of a maximum of the spectrum within the evaluation window. Subsequently, a corrected wavelength axis is determined for each acquired spectrum, and this adaptation is followed by averaging the measurements.

According to an advantageous overall design, the fluid analysis system according to the invention includes a sensor module, into which at least one spectrometer according to the invention is integrated, and an analysis unit. The sensor module can be fixed in an analysis unit using a locking clamp, whilst at the same time electrical and fluid connections can be made. As a result, the installation and the connection of the sensor module are substantially simplified.

DETAILED DESCRIPTION OF PREFERRED EMBODIMENTS

Figure 1:
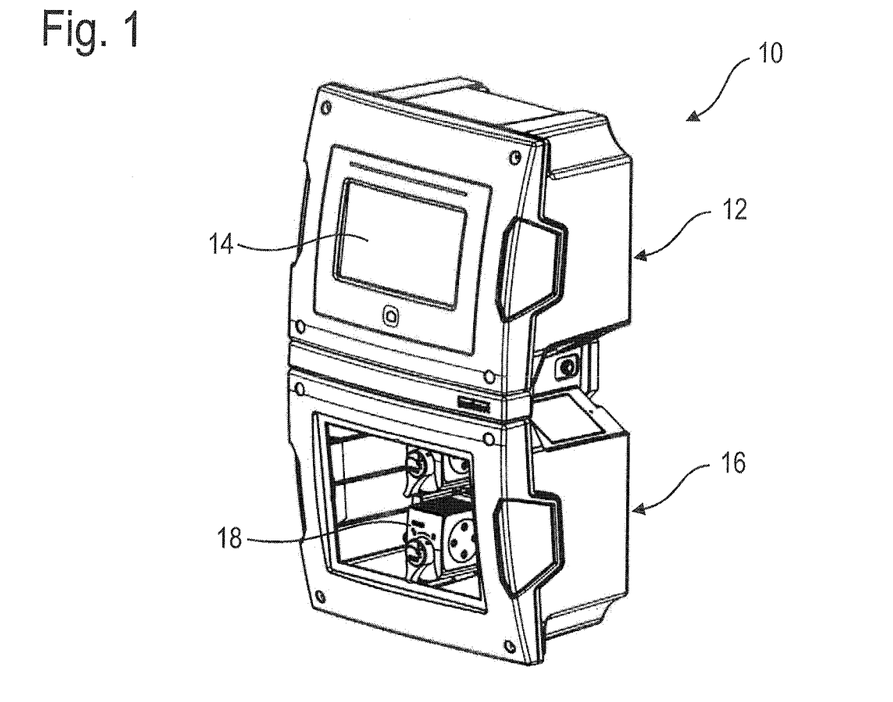
FIG. 1 shows a perspective view of a modular fluid analysis system having a sensor module according to the invention.
Figure 2:
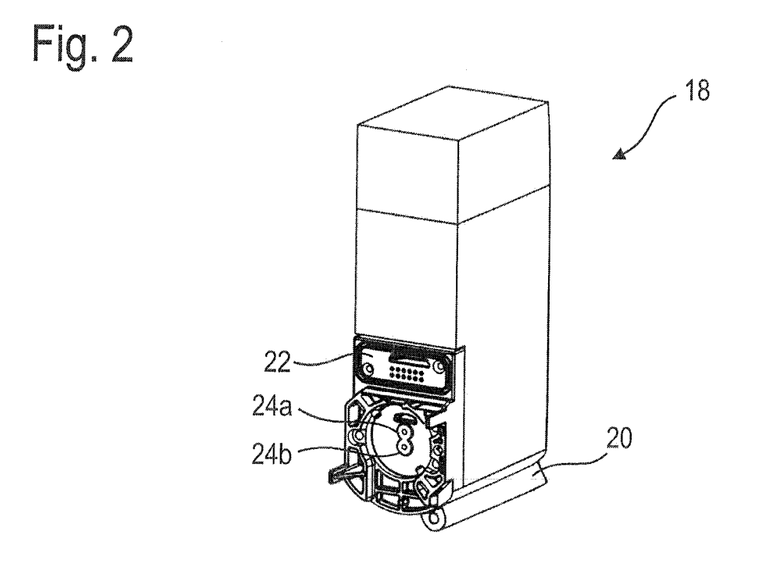
FIG. 2 shows a perspective view of a sensor module according to the invention.

FIG. 1 shows a fluid analysis system 10 of a modular design, which comprises an electronic unit, here in the form of an electronic module 12 with a display 14, and an analysis unit, here in the form of an analysis module 16. One or more sensor modules 18 can be installed in the analysis module 16. The installation is done in a simple manner using a locking clamp 20 mounted on the sensor module 18. When the locking clamp 20 is locked, apart from the sensor module 18 being fixed in the analysis module 16, all the required electrical and fluid connections are made at the same time. A single sensor module 18 with the corresponding electronic connections 22 and fluid connections 24a, 24b is shown in FIG. 2.

Figure 3:
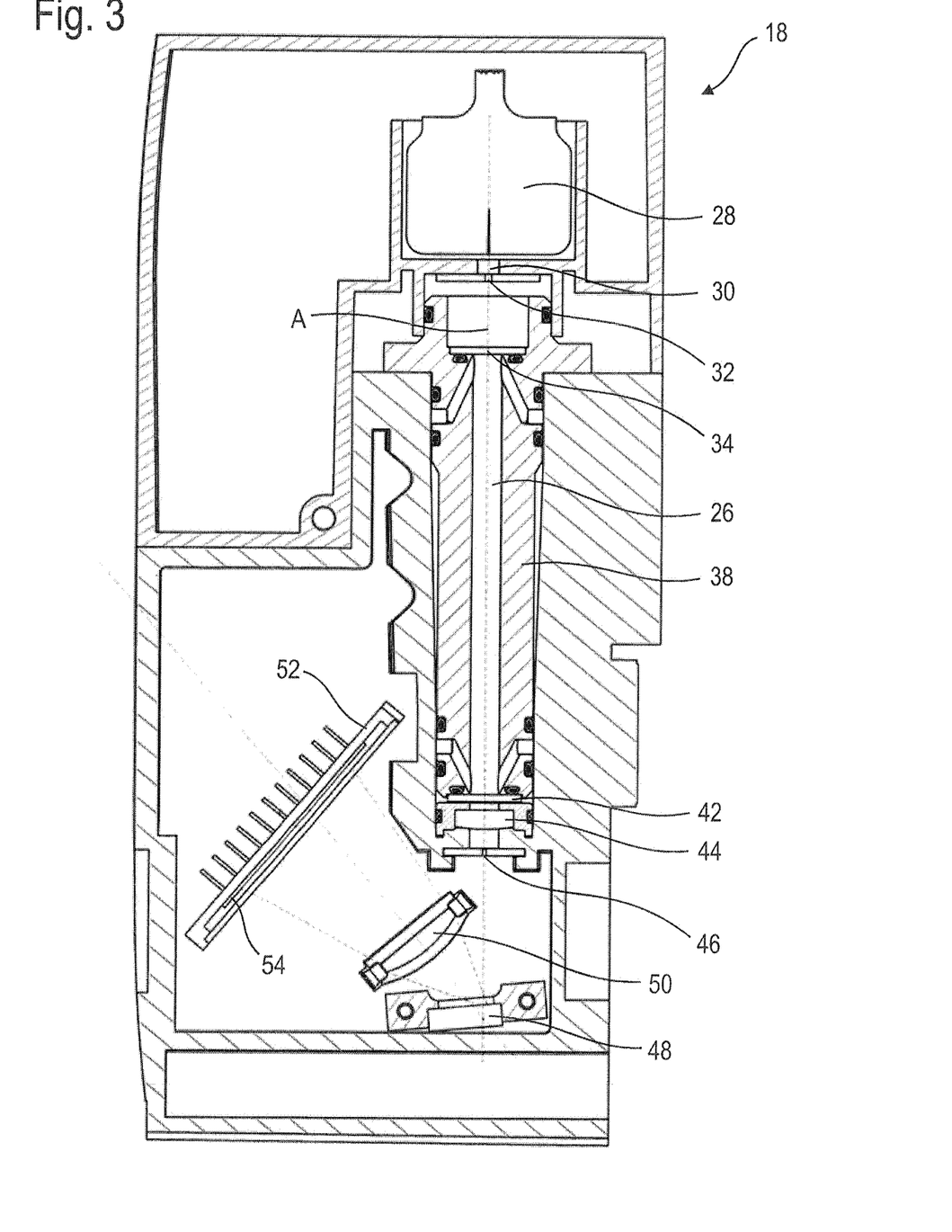
FIG. 3 shows a sectional view of a sensor module according to the invention with a spectrometer according to the invention.

It can be seen in FIG. 3 that a compact spectrometer is accommodated in the sensor module 18. The spectrometer is used for examining a fluid that can flow into and out of a sample chamber 26 via channels (not shown in FIG. 3).

The radiation source 28 of the spectrometer is chosen according to the type of analysis desired. For example, a low pressure mercury vapor lamp may be provided, which radiates UV light with a primary peak at 254 nm, or a xenon flash lamp, the light of which spans the range from UV (from approx. 190 nm) into infrared (up to approx. 2000 nm). For the sake of simplicity, the term "light" will be used here even if the emitted radiation of the radiation source 28 falls outside of the visible range.

A small inlet window 30 of the otherwise shielded radiation source 28 and an entrance aperture (referred to below as first aperture) 32 of the spectrometer define an optical axis A. The width of the entrance aperture 32 is in the (sub) millimeter range, for example in the range between 0.1 and 1.0 mm.

The light then enters, through an end-side entrance window 34 that is transparent for light of the radiation source 28, into the sample chamber 26 in which the fluid to be examined is present.

The sample chamber 26 is elongated, with a dimension along the optical axis A being in the order of magnitude of several centimeters, for example 6 cm. Such a length in the direction of the beam path is required if the substances to be detected are present in the fluid only in low concentrations.

Figure 4:
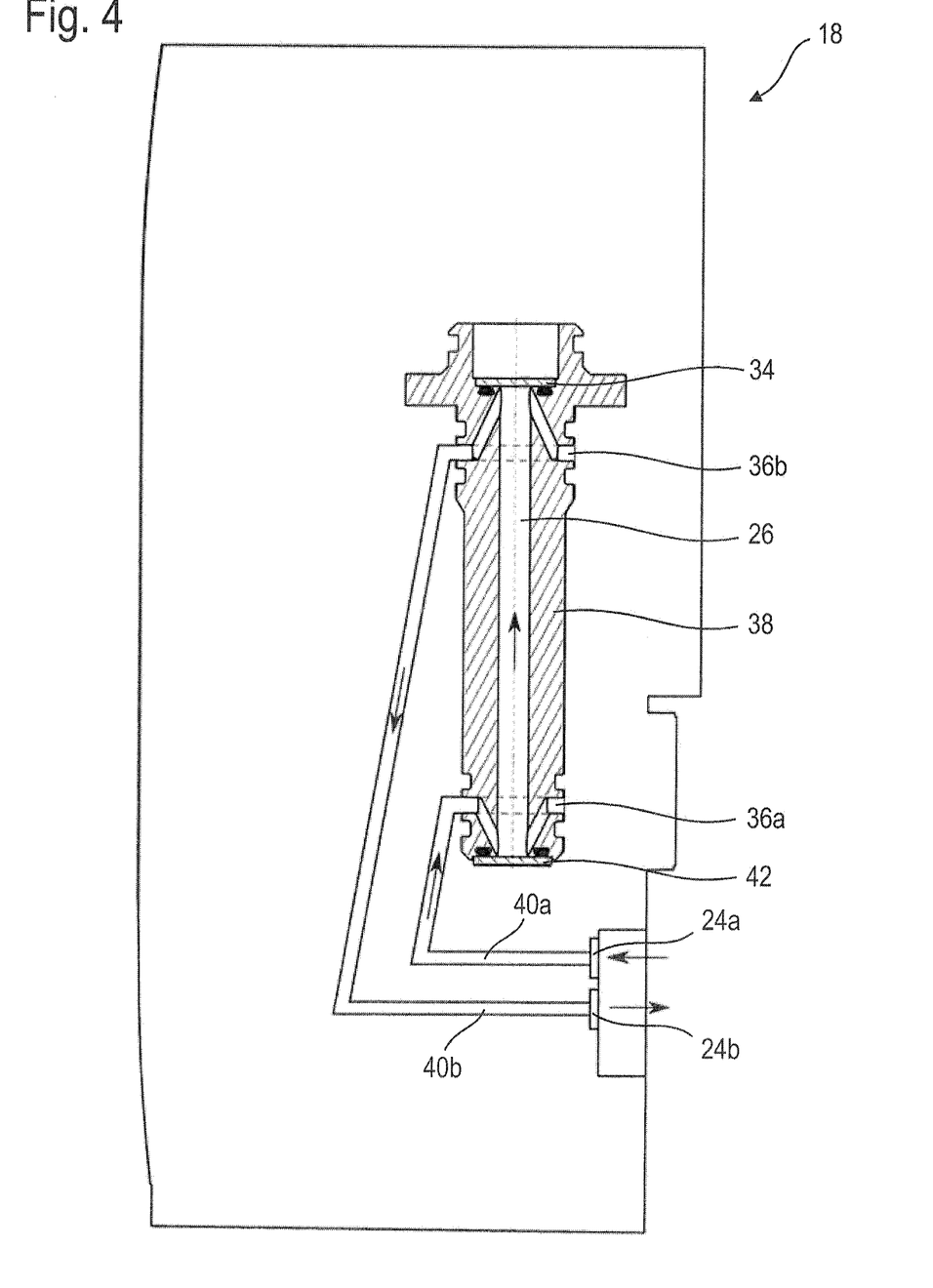
FIG. 4 shows an example of the flow profile of the fluid to be examined in the sensor module.

The sample chamber 26 may be the inside of a cuvette or of another housing that surrounds a fluid channel. FIG. 4 shows an example of the inflow and outflow of the fluid in such a housing 38 via ring lines 36a, 36b. For better clarity, this figure only shows the fluid connections 24a, 24b, the inflow channel 40a and the outflow channel 40b as well as the housing 38 with the entrance window 34 and the end-side exit window 42 provided at the opposite end, through which the light from the sample chamber 26 is coupled out along the optical axis A.

In order to minimize influences from scattered light, the housing 38 that surrounds the sample chamber 26 is as opaque as possible which, in the case of a (semi)transparent housing material, can be achieved for example by a coating. This does of course not apply to the areas of the entrance window 34 and the exit window 42.

In any case, the sample chamber 26 is integrated into the spectrometer in order to reduce the size, i.e. the sample chamber 26 is not located in front of, but behind the entrance aperture 32 of the spectrometer.

The light coupled out of the sample chamber 26 passes through a collimator lens (first lens) 44 and an additional restriction aperture (referred to below as second aperture) 46. The focal length of the collimator lens 44 is in the centimeter range, for example 5 cm.

As shown in FIG. 3, the second aperture 46 is preferably located in the area of the beam, in which the rays are collimated by the first lens 44, i.e. the rays basically run parallel. However, the second aperture 46 may, if viewed in the direction of the beam path, be mounted just in front of the first lens 44, which will be explained in more detail below.

Figure 8A:
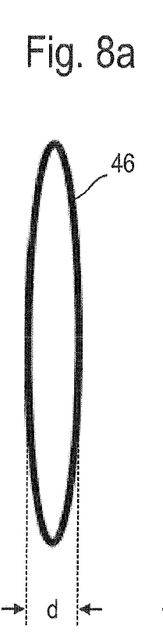
FIGS. 8a to 8f show various embodiment examples of the geometrical shape of the second aperture.
Figure 8B:
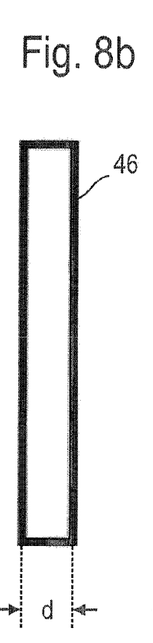
Figure 8C:
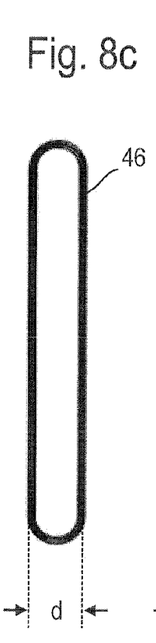
Figure 8D:
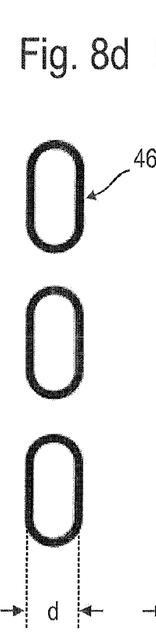
Figure 8E:
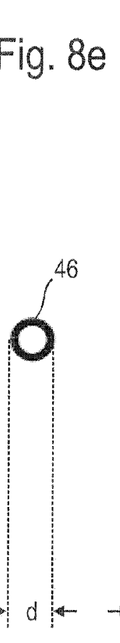
Figure 8F:
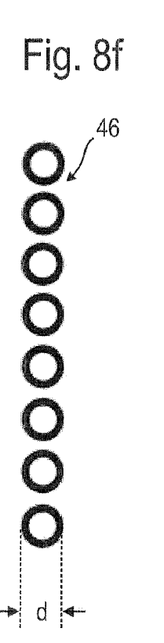

The second aperture 46 is preferably formed as a narrow gap, the longitudinal direction of which would run perpendicularly to the paper plane in FIG. 3. The maximum extension of the gap perpendicularly (transversely) to the longitudinal direction defines the width d of the second aperture 46 (see e.g. FIG. 8a), which is in the (sub)millimeter range, for example in the range between 0.1 and 1.0 mm. The possible geometrical shapes of the second aperture 46 will also be explained in more detail below.

Once the light has been split up into its spectral colors by a diffraction element 48 in the form of a reflection grating, a transmission grating or a prism, it is focussed onto a detector 52 that is light-sensitive to the relevant wavelength range, by a focussing lens (second lens) 50. The focal length of the focussing lens 50 is again in the centimeter range, for example 3.6 cm.

The diffraction element 48 is preferably formed as a mirror grating, so that the detector 52 does not need to be located in the extension of the optical axis A, but may be mounted in a space-saving manner in a free space of the sensor module 18 next to the sample chamber 26. The diffraction element 48 can also be coated as a diffraction grating with a suitable gap geometry or may be formed to be only as narrow as a gap would be wide.

The detector 52 is preferably a space-saving line sensor with a one-dimensional array of suitable detector elements. The length of the optically sensitive area in the detector plane 54 is in the centimeter range, for example 2.54 cm. The electric signals of the detector 52 are processed in an evaluation unit of the sensor module 18 and/or of the electronic module 12 of the fluid analysis system 10. The measurement results are indicated on the display 14 of the electronic module 12.

The significance of the second aperture 46 for the quality of the measurement results will be explained in more detail below. To this end, reference is first made to the beam path shown in FIG. 5, in which no second aperture is present. In particular, if low-cost components (entrance aperture 32, lenses 44, 50, diffraction element 48) are used and a compact design of the spectrometer is chosen, such a constellation will lead to an extensive curvature of the image field 56. Here, the image field 56 is the surface on which the fanned-out (expanded) spectrum of the light is in sharp focus.

Figure 5:
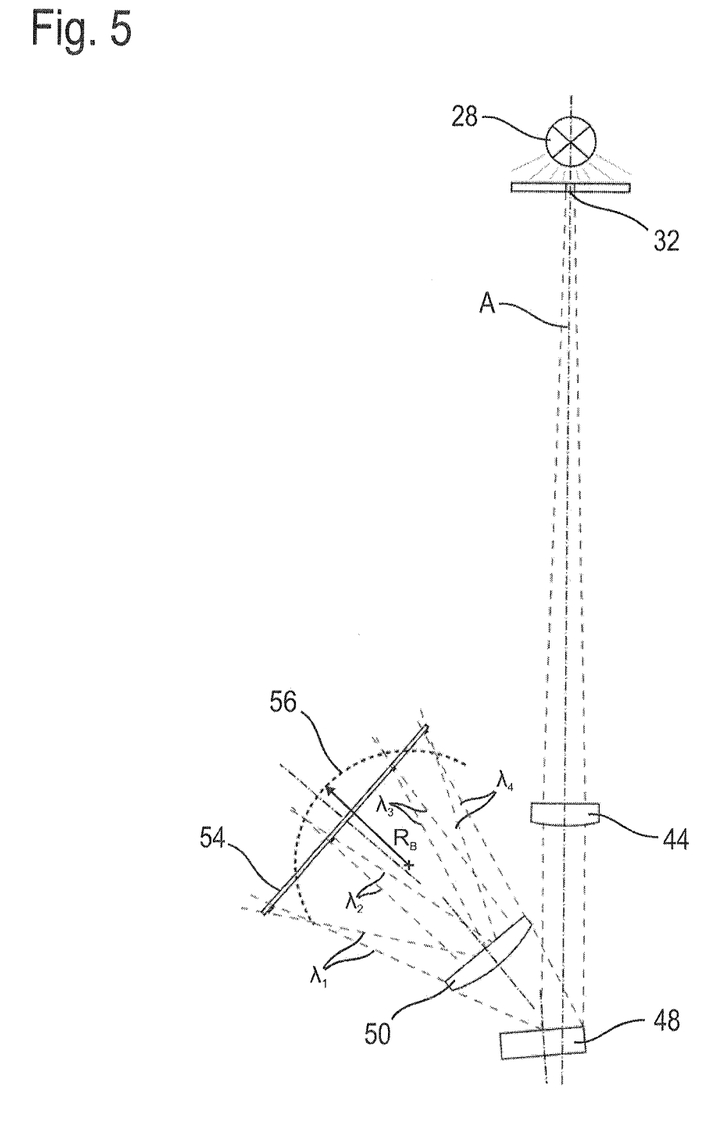
FIG. 5 shows the beam path through a spectrometer not in accordance with the invention without a second aperture.

The radius $R_B$ of the image field 56 can be mathematically derived in a known manner from the focal length and the refractive index of the lenses 44, 50 by calculating the so-called Petzval sum. The Petzval sum is generally defined as follows:

$$\frac{1}{r_p} = \sum_i \frac{1}{n_i f_i}$$

wherein $f_i$=focal length and $n_i$=refractive index of the respective lens.

The inverse value of the Petzval sum $r_p$ corresponds to the desired image field radius $R_B$.

As has already been mentioned, due to the small dimensions of the spectrometer and the small focal lengths required as a result, which in turn means small lens radii, the curvature of the image field 56 is relatively extensive.

According to the exemplary values mentioned above, assuming a refractive index of n=1.54 of the two lenses 44, 50 for the image field radius $R_B$, a value of 32 mm would result. Such a curvature, however, does not go together with a planar arrangement of the detector elements of the line sensor (detector plane 54).

As can be seen in FIG. 5, the detector plane 54 and the image field 56 coincide only in two locations, i.e. the resolution is suboptimal in all other locations. The stronger the curvature of the image field 56 is, the more blurred the image on the detector 52 will be. In FIG. 5, this is shown by way of example for four wavelengths $\lambda_1$, $\lambda_2$, $\lambda_3$ and $\lambda_4$ selected at random.

Whilst a high resolution for individual narrow spectral ranges that are of particular interest can be achieved by way of an appropriate positioning of the detector 52 relative to the image field 56, however, this is not sufficient for most practical applications, especially if high demands on the measurement result are made.

Figure 6:
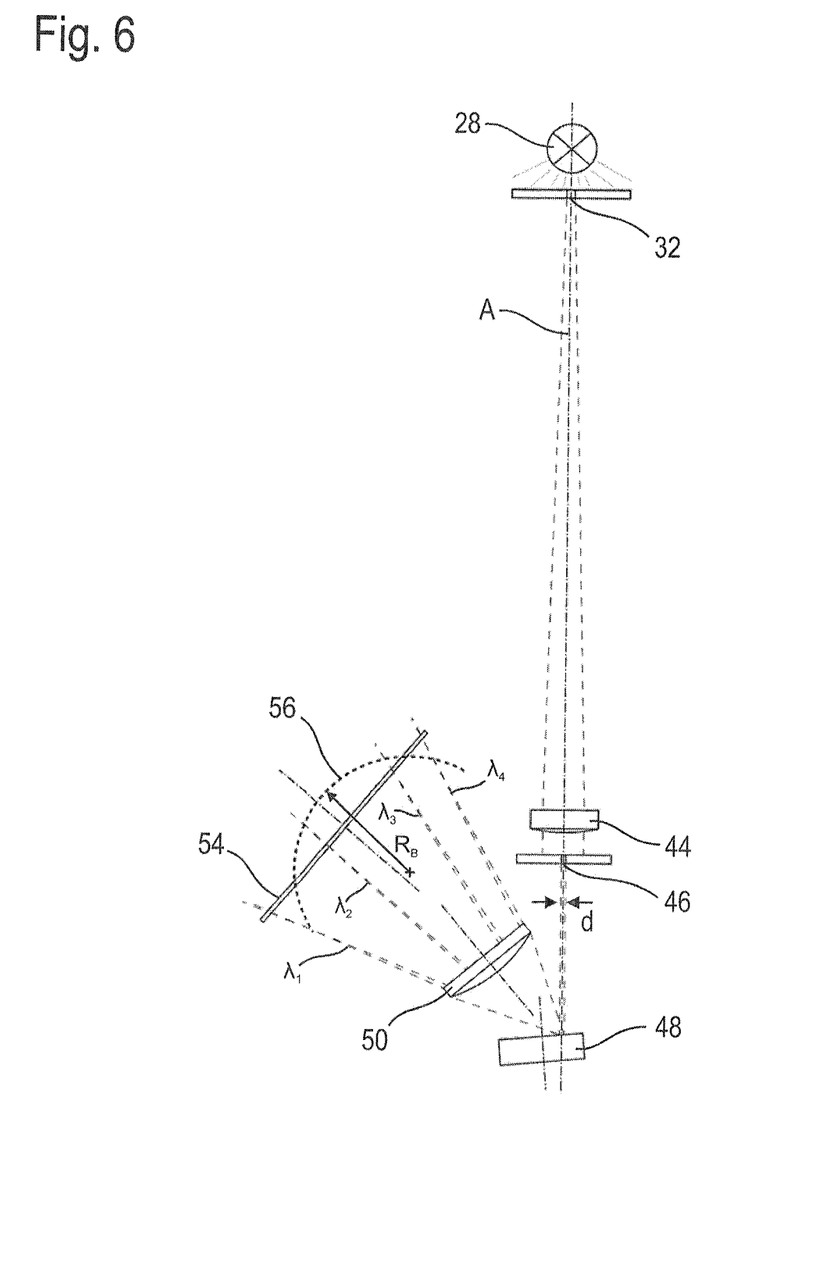
FIG. 6 shows the beam path through a spectrometer according to the invention with a second aperture.

In order to allow a resolution as high as possible over a wide range of the spectrum, i.e. in order to minimize blur of the remaining wavelength ranges, the second aperture 46 is provided. FIG. 6 shows the beam path through the spectrometer with the second aperture 46. As can be seen there, the width d of the second aperture 46 is considerably smaller than the diameter D of the collimator lens 44.

It can be seen from a comparison between FIG. 5 and FIG. 6 that the second aperture 46 allows the light beam, rectified by the collimator lens 44, to be incident on just a very narrow part of the diffraction element 48, i.e. the maximum diameter of the light beam in the direction perpendicular to the optical axis A in the paper plane of FIG. 6 is greatly limited by the second aperture 46. In other words: the effective diameter of the light beam is reduced to the width d of the second aperture 46. As a result, the optical errors occurring as a result of the image field curvature are substantially restricted in the detector plane 54. This can be seen, by way of example, in the wavelengths $\lambda_1$, $\lambda_2$, $\lambda_3$ and $\lambda_4$, all of which are imaged in very sharp focus.

It is obvious that the sharpness of the entire image is increased as the aperture width d decreases. Quantitatively, this can be expressed by means of a focussing factor S, which can be defined as follows:

$$S=R_B/d$$

wherein $R_B$=image field radius and d=width of the second aperture.

In any case, the sharpening factor S should be greater than 10; the target is a value in the range between 30 and 70.

FIGS. 7a to 7f show alternative embodiments or arrangements of the second aperture 46 in relation to the collimator lens 44 between the sample chamber 26 and the diffraction element 48. In principle, the second aperture 46 may be placed either behind or immediately in front of the collimator lens 44. In the first case, i.e. when the second aperture 46 is disposed in the area in which the light is collimated (Fourier space), the distance between the second aperture 46 and the collimator lens 44 or the diffraction element 48 may in practice be chosen as desired. In the second case, the second aperture 46 should be placed as closely as possible in front of the collimator lens 44.

Figure 7A:
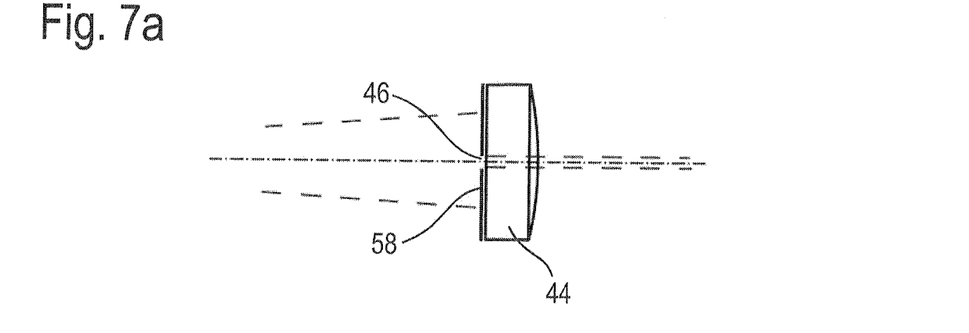
FIGS. 7a to 7f show further installation and embodiment examples of the second aperture.

According to FIG. 7a, an opaque layer 58 is applied on the side of the collimator lens 44 that faces the sample chamber 26, e.g. by way of vapor deposition. In layer 58, a small opening is provided as a second aperture 46 at the intersection with the optical axis A.

Figure 7B:
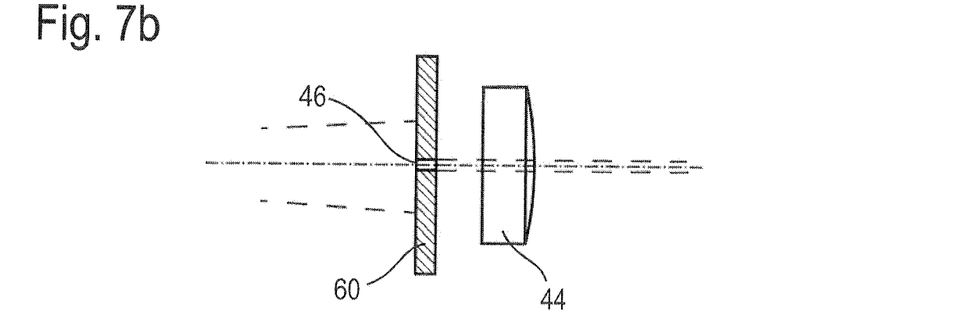

In FIG. 7b, the second aperture 46 is shown in a separate component 60 disposed just in front of the collimator lens 44.

Figure 7C:
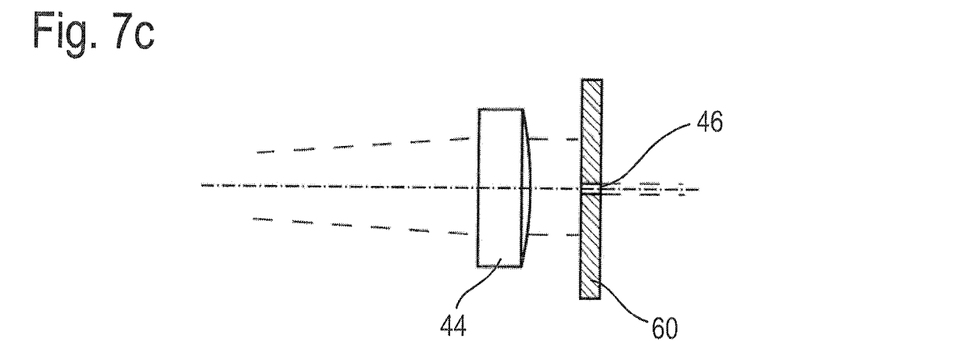

The latter also applies to FIG. 7c, with the exception that the second aperture 46 is here disposed behind the collimator lens 44. As has already been mentioned, the distance from the collimator lens 44 is not critical here.

Figure 7D:
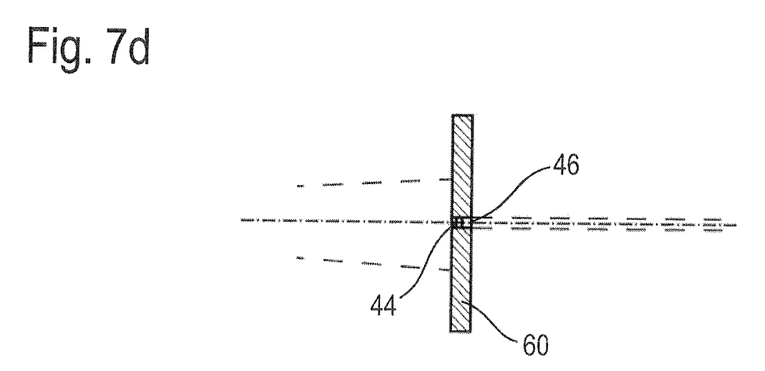

In the embodiment of FIG. 7d, an extremely small collimator lens 44 is provided which is held in a component 60. The second aperture 46 is here determined by the holder that directly surrounds the collimator lens 44.

Figure 7E:
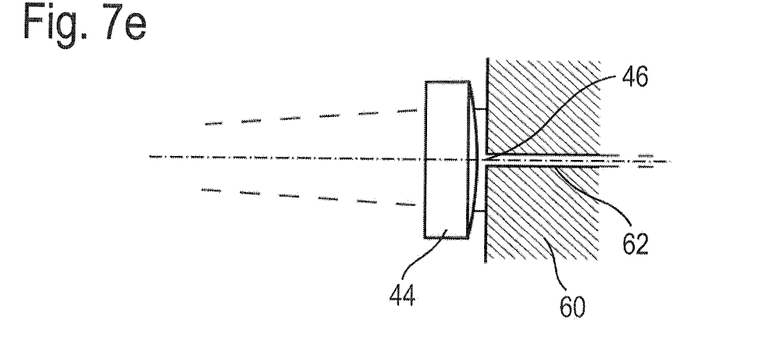

In FIG. 7e, the second aperture 46 is determined by a narrow light channel 62 in a component 60 disposed behind the collimator lens 44, which component can also be used for holding the collimator lens 44.

Figure 7F:
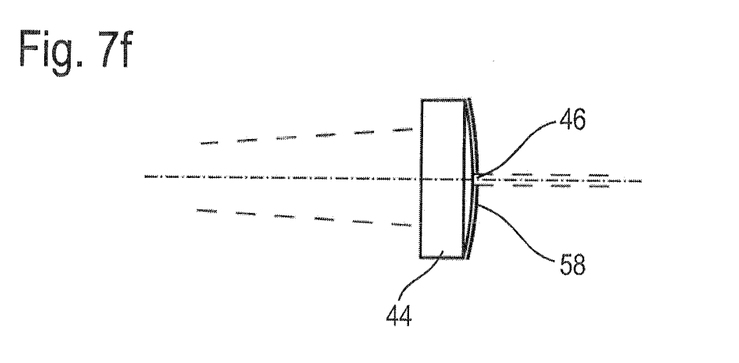

As shown in FIG. 7f, an opaque layer 58 may be applied, analogously to the embodiment according to FIG. 6a, also on the side of the collimator lens 44 that faces the diffraction element 48, which layer has a small opening as a second aperture 46 at the intersection with the optical axis A.

FIGS. 8a to 8f show possible geometric shapes of the second aperture 46. Apart from the slit-shaped embodiments, also circular or other oval, but also square, rectangular or other polygon-shaped embodiments are possible, if necessary in a larger number as a linear array. However, in all cases it is predominantly the aperture width d that is responsible for the sharpness of the image, which aperture width is the same size in all the embodiments shown. In all of the embodiments shown in FIGS. 8a to 8f, the second aperture 46 is always arranged, in a design according to FIG. 3 or a similar design, so that the aperture width d lies in a direction perpendicular to the optical axis A in the paper plane (cf. FIG. 6). This means that the light beam, after passing through the second aperture 46, is smaller in this direction than in the direction perpendicular thereto (such as for example in the embodiments according to FIGS. 8a to 8d and 8f). However, the "effective" diameter of the light beam is always the diameter in the direction of the aperture width d.

Figure 9:
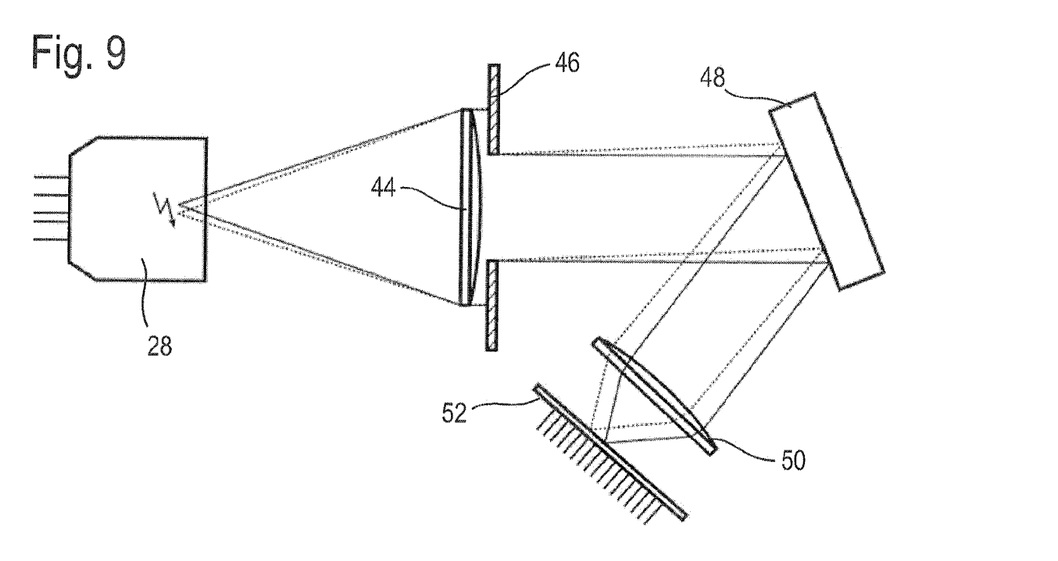
FIG. 9 shows two beam paths through a spectrometer according to the invention, shown in a simplified manner, according to an alternative type of design.

FIG. 9 shows, in a simplified manner, an alternative type of design of the spectrometer described above, in which no entrance aperture 32 is provided between the radiation source 28 and the sample chamber 26. Whilst this simplified design has the advantage that there is no assembly effort needed for the exact alignment of the entrance aperture 32 relative to the radiation source 28, however, because of the absence of the entrance aperture 32 it is no longer ensured that the light of the radiation source 28 always enters into the spectrometer at exactly the same location.

In this respect, FIG. 9 shows an example of the beam path of a wavelength in a first measurement (solid line) and in a second measurement (dotted line). It can clearly be seen that in the case of the second measurement, the point of incidence on the sensor of the detector 52 has shifted relative to the first measurement. As a result of the "jumping" of the arc of the radiation source 28, the entire spectrum acquired by the sensor of the detector 52 is shifted.

It will be described below how the missing entrance aperture 32 and the alignment thereof are "replaced" with a computational procedure.

If, as described above, a xenon flash lamp is used as the radiation source 28, then the flash arc (light arc) thereof is basically used as an entrance gap of the spectrometrical design, which will be briefly explained below. Many radiation sources emit a characteristic spectrum with maxima at known and exactly defined wavelengths. These characteristic maxima may also be used for the initial calibration of the spectrometer. The sensor of the detector 52, on which e.g. 3,600 pixels are located, can merely detect the brightness of each individual pixel and is per se "color-blind". It is only as a result of the association of the individual pixels to respectively one defined wavelength that the brightness can be measured in various wavelength ranges. The initial calibration is carried out by way of the association of a characteristic maximum with a pixel of the sensor. All further pixels are permanently associated on the basis of this "calibration pixel" from the corresponding wavelengths. Thus, a calibrated spectrometer is realized.

Since the arc in the radiation source 28 is not stationary, the acquired spectrum on the sensor will also jump accordingly. More specifically, as a result of the position fluctuations of the flash, the spectrum has shifted from one measurement to the next by several pixels on the sensor. As a consequence, the association of the wavelengths with the pixels will deviate from the actual calibration. Ideally, each measurement is individually calibrated or corrected on the basis of a selected characteristic range (evaluation window). However, simple averaging by adding up will result in loss of detail or in a deteriorated resolution; the spectrum becomes "blurred".

Figure 10:
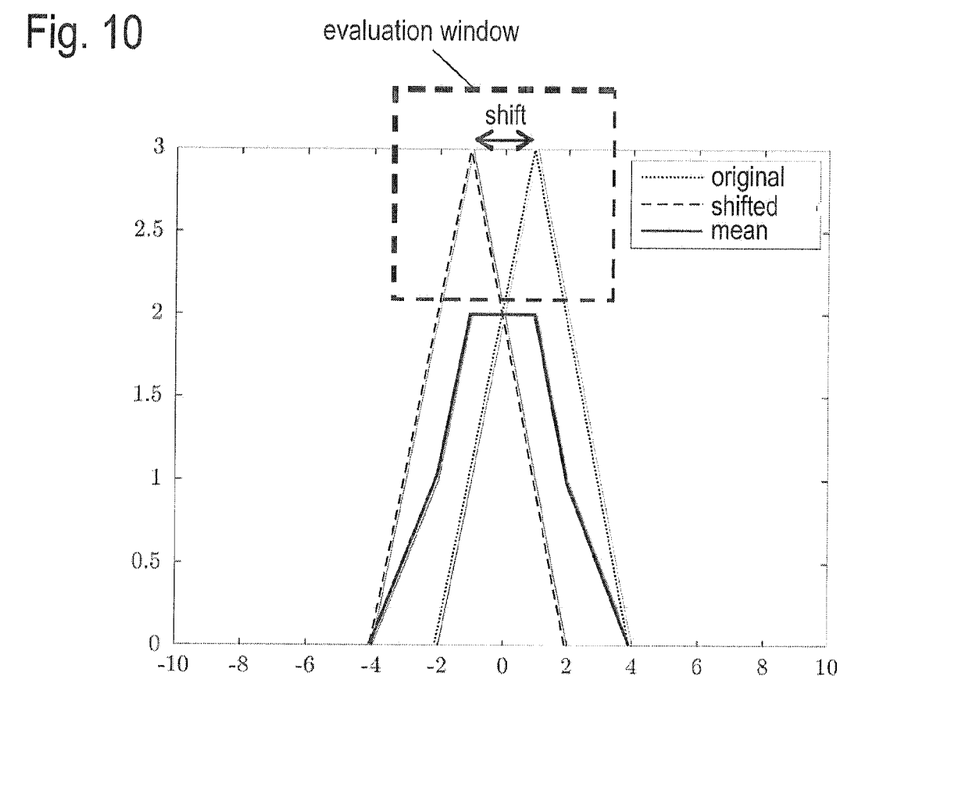
FIG. 10 shows a schematic view of a detail of two spectra acquired by the detector as consecutive measurements.

The problem is schematically illustrated in FIG. 10. The dotted line corresponds to the first measurement in a series of measurements (original). The dashed line corresponds to the subsequent measurement (shift). A simple summation of the measurements results in the mean value (mean) shown as a solid line. Here, essential information of the series of measurements gets lost and the resolution of the spectrometer deteriorates.

Figure 11:
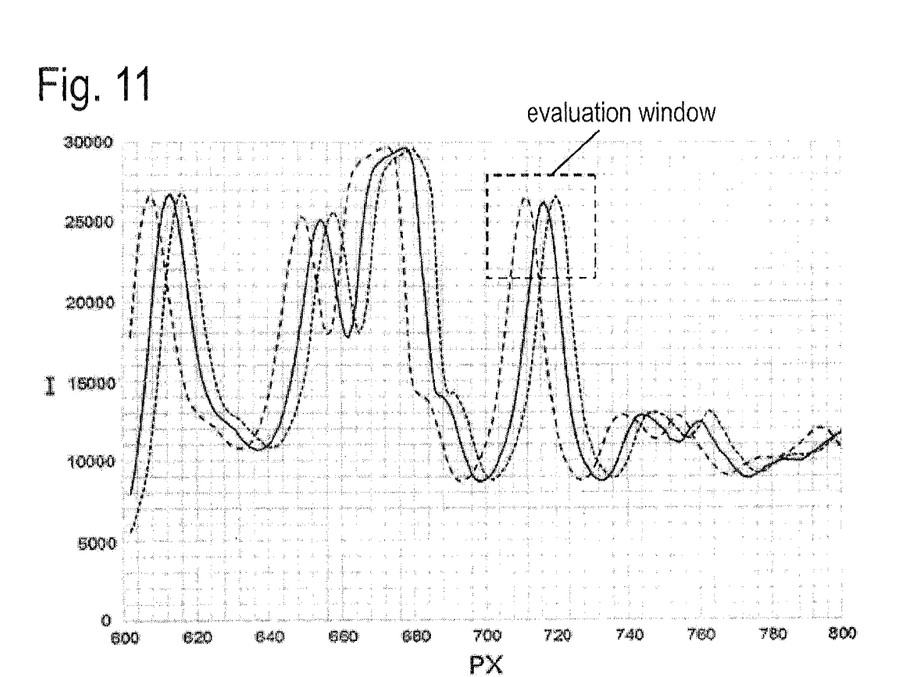
FIG. 11 shows three measured spectra in a diagram in which the light intensity is plotted over the pixel position of the detector sensor.

FIG. 11 shows three real measurements with different lines (solid, dotted, dashed) in a diagram. The evaluation window is located in an area in which an easily identifiable characteristic peak of the spectrum must lie—despite a possible shift.

The problem explained above is solved by observing and averaging the measurements relative to each other, taking into account the shift, in the course of the evaluation. The shift can be calculated for example on the basis of the position of the maximum. In doing so, a corrected wavelength axis is determined for each spectrum and the respective spectrum will not be added until after the adaptation.

Figure 12:
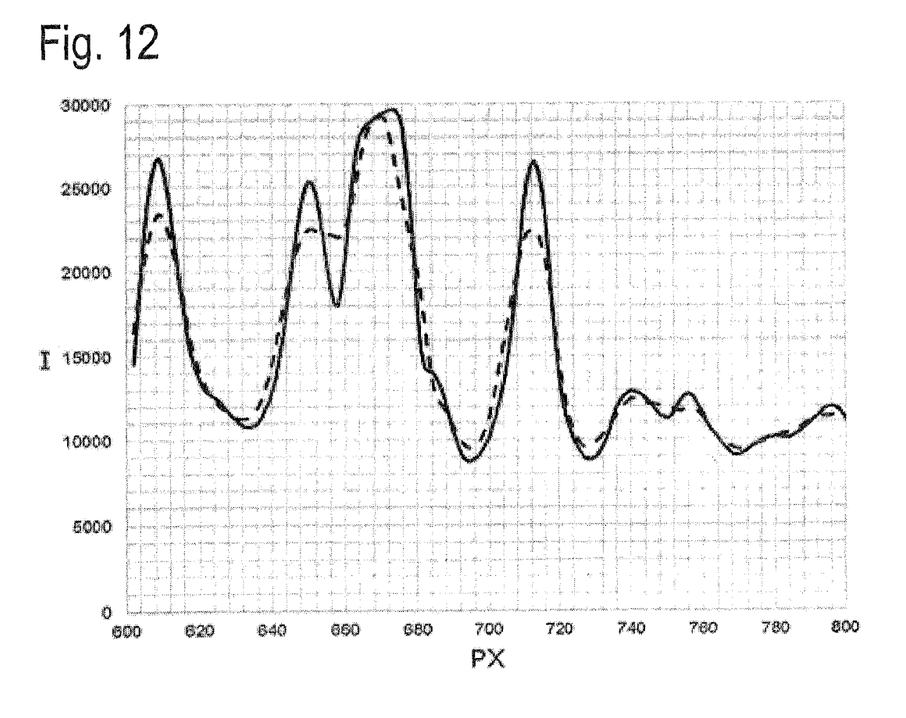
FIG. 12 shows an averaged spectrum plotted in on the diagram without a correction of the y axis, and an averaged spectrum with a corrected y axis.

The improved result of this method can be seen in FIG. 12, in which an averaged spectrum is shown once without taking into consideration the shift, i.e. without a correction of the y axis (with a pixel shift), with a dashed line and once under consideration of the shift, i.e. with a corrected y axis (with a pixel shift).

The process of the computational correction will be outlined below. The adoption of a spectrum includes the search for the characteristic point within the determined evaluation window, in which a characteristic range of the spectrum of the radiation source 28 will always be present. As indicated in FIG. 10, the evaluation window is defined by an extension in the x direction and an extension in the y direction. The extension in the x direction corresponds to a wavelength or pixel range, whereas the extension in the y direction (intensity) is useful for ensuring secure identification of a characteristic location. The maximum value—within certain tolerances—is known. The evaluation window increases the certainty of a measurement altogether. It is selected such that the characteristic point will always be present in this area and will be uniquely identifiable. The position of the first characteristic point is stored as a reference for a series of measurements.

Subsequently, further spectra are acquired and the characteristic point is searched in each case. The shift between the currently determined characteristic point and the reference of the series of measurements is calculated. Subsequently, the shifted spectra are added.

The next step is the formation of a mean value. On this basis, the pixels of the sensors are associated with a specific wavelength and further, application-specific calculations are carried out using the averaged series of measurements.

Subsequently, reference is briefly made to the particularities of the characteristic point. This is a property of the radiation source (peak in the spectrum) that is independent of the sample to be examined. (In other applications also a characteristic property of the sample could in principle be used that remains unchanged.) The characteristic point has a very high likelihood of occurrence (close to 100%), irrespective of the sample to be examined. The characteristic point constitutes a known position within a defined evaluation window.

LIST OF REFERENCE NUMERALS

10 Fluid analysis system
12 Electronic module
14 Display
16 Analysis module
18 Sensor module
20 Locking clamp
22 Electronic connections
24a Fluid connection
24b Fluid connection
26 Sample chamber
28 Radiation source
30 Inlet window
32 Entrance aperture (first aperture)
34 Entrance window
36a Ring line
36b Ring line
38 Housing
40a Inflow channel
40b Outflow channel
42 Exit window
44 First lens (collimator lens)
46 Restriction aperture (second aperture)
48 Diffraction element
50 Second lens (focussing lens)
52 Detector
54 Detector plane
56 Image field
58 Layer
60 Component
62 Light channel
A Optical axis
d Width of the second aperture
$R_B$ Radius of the image field
$r_p$ Inverse value of the Petzval sum
f Focal length
n Refractive index
λ Wavelength
D Diameter of the first lens
S Sharpening factor

The invention claimed is:

1. A spectrometer, in particular for being installed in a sensor module, comprising a radiation source and the following components defining a beam path or being arranged along the beam path:

a sample chamber for a fluid to be examined, a first lens,
a diffraction element,
a second lens, and
a detector,
   wherein a restriction aperture for restricting the effective diameter of the light beam incident on the diffraction element is provided between the first lens and the diffraction element, and wherein the light beam is not focused at any point before reaching the diffraction element.

2. The spectrometer according to claim 1, wherein the width (d) of the restriction aperture is considerably smaller than the diameter of the first lens.

3. The spectrometer according to claim 1, wherein the width (d) of the restriction aperture is in a range of between 0.1 and 1.5 mm.

4. The spectrometer according to claim 1, wherein the focal length of the first lens is in a range of between 3 and 7 cm, and/or in that the focal length of the second lens is in the range of between 2 and 5 cm.

5. The spectrometer according to claim 1, wherein a sharpening factor defined as S=RB/d, wherein RB=image field radius and d=width of the restriction aperture, is greater than 10.

6. The spectrometer according to claim 1, wherein the restriction aperture is located in a Fourier space, in which the light of the radiation source is collimated.

7. The spectrometer according to claim 1, wherein the restriction aperture is formed by a narrow light channel in a component that is also used as a holder for the first lens.

8. The spectrometer according to claim 1, wherein the restriction aperture is formed in a layer that is applied on the side of the first lens that faces the diffraction element.

9. The spectrometer according to claim 1, wherein the detector is a linear detector, in particular a linear sensor.

10. The spectrometer according to claim 1, wherein the maximum extension of the optically sensitive area of the detector is in the range of between 1 and 4 cm.

11. The spectrometer according to claim 1, wherein the sample chamber has a length of several more than 4 cm, in the direction of the beam path.

12. The spectrometer according to claim 1, wherein the sample chamber is connected to an inflow channel and an outflow channel, which open into the sample chamber via ring lines, wherein the ring lines are formed in a housing that surrounds the sample chamber.

13. The spectrometer according to claim 1, wherein the diffraction element is formed as a mirror grating.

14. The spectrometer according to claim 1, wherein the radiation source is a xenon flash lamp.

15. The spectrometer according to claim 1, wherein an entrance aperture is additionally provided in the beam path.

16. The spectrometer according to claim 1, wherein the sample chamber is provided in the beam path behind the entrance aperture.

17. The spectrometer according to claim 1, wherein the sensor comprises a one-dimensional array of detector elements.

18. A fluid analysis system comprising a spectrometer according to claim 1.

19. A fluid analysis system comprising a spectrometer according to claim 1, wherein no entrance aperture is provided between the radiation source and the sample chamber, wherein the fluid analysis system further comprises an electronic unit that is configured to take into account a shift of the spectra acquired by the detector during an evaluation of multiple measurements.

20. The fluid analysis system according to claim 19, wherein the electronic unit is configured such that an initial calibration is carried out by associating a characteristic maximum of the spectrum with a pixel of a sensor of the detector, and in that on the basis of this pixel, further pixels of the sensor are permanently associated with corresponding wavelengths.

21. The fluid analysis system according to claim 20, wherein the electronic unit is configured such that each measurement is individually calibrated and/or corrected on the basis of a selected characteristic range of the detected spectrum in the form of an evaluation window, which is defined by a wavelength range or a pixel range of the sensor which corresponds to the wavelength range, and by an intensity range.

22. The fluid analysis system according to claim 21, wherein the electronic unit is configured such that a shift between various measurements is calculated on the basis of the position of a maximum of the spectrum within the evaluation window, a corrected wavelength axis is determined for each acquired spectrum, and this adaptation is followed by averaging the measurements.

23. The fluid analysis system, comprising a sensor module having installed therein at least one spectrometer according to claim 1, and an analysis unit, the fluid analysis system further comprising a locking clamp that can be used to fix the sensor module in the analysis unit whilst at the same time electrical and fluid connections are made.

24. A spectrometer, in particular for being installed in a sensor module, comprising a radiation source and the following components defining a beam path or being arranged along the beam path:
   a sample chamber for a fluid to be examined,
   a first lens,
   a diffraction element,
   a second lens, and
   a detector,
   wherein a restriction aperture for restricting the effective diameter of the light beam incident on the diffraction element is provided in the beam path immediately in front of the first lens, and wherein the light beam is not focused at any point before reaching the diffraction element.

25. The spectrometer according to claim 24, wherein the restriction aperture is formed in a layer applied on the side of the first lens that faces the sample chamber.

26. The spectrometer according to claim 24, wherein the restriction aperture is formed by a holder that immediately surrounds the first lens.

* * * * *